(12) United States Patent
Tornier et al.

(10) Patent No.: US 9,872,687 B2
(45) Date of Patent: Jan. 23, 2018

(54) DRIVING ASSEMBLY FOR A CUTTING TOOL OF THE SHAVER TYPE

(71) Applicant: CLARIANCE, Dainville (FR)

(72) Inventors: Alain Tornier, Saint Ismier (FR); Guy Viart, Saint Leger (FR); Jean Yves Leroy, Campagne-les-Hesdin (FR); Adrien Billon, Rochin (FR); Brice Krier, Dainville (FR); Sebastien Shuller, Strasbourg (FR); Afshin Gangi, Lahr (DE); Orlando Ortiz, New York, NY (US)

(73) Assignee: CLARIANCE, Dainville (FR)

( * ) Notice: Subject to any disclaimer, the term of this patent is extended or adjusted under 35 U.S.C. 154(b) by 1196 days.

(21) Appl. No.: 13/946,193

(22) Filed: Jul. 19, 2013

(65) Prior Publication Data

US 2014/0025079 A1    Jan. 23, 2014

Related U.S. Application Data

(60) Provisional application No. 61/673,288, filed on Jul. 19, 2012.

(51) Int. Cl.
*A61B 17/16* (2006.01)
*A61B 17/17* (2006.01)

(52) U.S. Cl.
CPC ...... *A61B 17/1671* (2013.01); *A61B 17/1617* (2013.01); *A61B 17/1642* (2013.01); *A61B 17/1644* (2013.01); *A61B 17/162* (2013.01); *A61B 17/1622* (2013.01); *A61B 17/1624* (2013.01); *A61B 17/1628* (2013.01); *A61B 17/1757* (2013.01)

(58) Field of Classification Search
CPC . A61B 17/16; A61B 17/1631; A61B 17/1646; A61B 17/1657; A61B 17/1671; A61B 2017/1648; A61B 2017/1651; A61B 2017/1653; A61B 17/32002; A61B 2017/320028; A61B 2017/320032; A61B 2017/32008; A61B 2017/320084
See application file for complete search history.

(56) References Cited

U.S. PATENT DOCUMENTS

| 5,201,731 | A | * | 4/1993 | Hakky | A61B 17/32002 600/461 |
| 5,403,276 | A | * | 4/1995 | Schechter | A61B 17/32002 604/118 |
| 5,490,860 | A | * | 2/1996 | Middle | A61B 17/32002 604/22 |
| 5,554,172 | A | * | 9/1996 | Horner | A61B 18/1402 606/22 |

(Continued)

*Primary Examiner* — Anu Ramana
(74) *Attorney, Agent, or Firm* — Young & Thompson

(57) ABSTRACT

The nucleotomy device makes it possible to produce a nuclear space Es in an intervertebral disc Di using a transosseous approach previously pierced in the body of a vertebra Va. The device includes a tool holder (2) provided with first connection elements (3) ensuring the placement of an electric rotary driving motor (4), second connection elements (5) for the placement of a blade cutting tool (6), driving elements (7) imparting rotational and longitudinal translational movements to the cutting tool (6), and injection and suction elements (8) making it possible to evacuate the debris from the nucleus resulting from cutting when it is formed inside the intervertebral disc.

21 Claims, 20 Drawing Sheets

(56) References Cited

U.S. PATENT DOCUMENTS

| | | | | |
|---|---|---|---|---|
| 5,643,304 A * | 7/1997 | Schechter | A61B 17/32002 | |
| | | | 604/22 | |
| 5,669,876 A * | 9/1997 | Schechter | A61B 17/32002 | |
| | | | 128/898 | |
| 5,685,877 A * | 11/1997 | Pagedas | A61B 18/1482 | |
| | | | 600/106 | |
| 6,090,103 A * | 7/2000 | Hakky | A61B 17/320758 | |
| | | | 604/20 | |
| 6,527,778 B2 * | 3/2003 | Athanasiou | A61B 10/0233 | |
| | | | 606/80 | |
| 6,602,248 B1 * | 8/2003 | Sharps | A01N 43/52 | |
| | | | 604/114 | |
| 7,670,328 B2 * | 3/2010 | Miller | A61B 10/025 | |
| | | | 604/187 | |
| 7,975,703 B2 * | 7/2011 | Jahns | A61B 18/14 | |
| | | | 128/898 | |
| 8,221,394 B2 * | 7/2012 | Andrew | A61B 17/3203 | |
| | | | 604/35 | |
| 8,715,287 B2 * | 5/2014 | Miller | A61B 10/025 | |
| | | | 606/80 | |
| 8,894,654 B2 * | 11/2014 | Anderson | B23B 49/02 | |
| | | | 173/176 | |
| 2003/0014047 A1 * | 1/2003 | Woloszko | A61B 18/148 | |
| | | | 606/41 | |
| 2010/0292684 A1 * | 11/2010 | Cybulski | A61B 18/14 | |
| | | | 606/33 | |
| 2011/0077674 A1 * | 3/2011 | Sullivan | A61B 17/32002 | |
| | | | 606/170 | |

* cited by examiner

DRIVING ASSEMBLY FOR A CUTTING TOOL OF THE SHAVER TYPE

FIELD OF THE INVENTION

The present invention relates to a nucleotomy device making it possible to produce a nuclear space in an intervertebral disc using a transosseous approach previously pierced in the body of a vertebra.

BACKGROUND OF THE INVENTION

Known from French patent no. 11/00199, belonging to the applicant, is a drill with a curved profile making it possible to produce the transosseous approach inside the body of a vertebra.

Also known from French patent no. 08/01860, belonging to the applicant, is a nucleus pulposus implant inserted inside a nuclear space formed in the intervertebral disc.

SUMMARY OF THE INVENTION

The nucleotomy device according to the present invention aims to allow the surgeon, after he has pierced one or two channels inside the body of the vertebra, to produce a nuclear space for placing a nucleus pulposus implant to repair a damaged intervertebral disc.

The nucleotomy device according to the present invention includes a tool holder provided with first connection means ensuring the placement of an electric rotary driving motor, second connection means for the placement of a blade cutting tool, driving means imparting rotational and longitudinal translational movements to the cutting tool, and injection and suction means making it possible to evacuate the debris from the nucleus resulting from cutting when it is formed inside the intervertebral disc.

The nucleotomy device according to the present invention includes adjustment means limiting the translational travel of the cutting tool inside the intervertebral disc.

The nucleotomy device according to the present invention includes means for retracting the cutting tool before it is inserted into the intervertebral disc.

The nucleotomy device according to the present invention includes a cutting tool that is made up of a flexible metal rod enclosed in a plastic protective sheath, a flexible link making it possible to link one of the ends of the metal rod to a bimetal knife made from a super-elastic material, a linking element linking the other end of the metal rod to the driving means of the tool holder, and a connection ring cooperating with the second connection means to immobilize said cutting tool on said tool holder.

The nucleotomy device according to the present invention includes a cutting tool whereof the connection ring cooperates with a clamping chuck making it possible to place and retain the protective sheath around the flexible metal rod.

The nucleotomy device according to the present invention includes a cutting tool whereof the flexible link of the cutting tool is made up of a torque cable fastened on the one hand to the bimetal knife and on the other hand to the metal rod, said torque cable being able to deformed to follow small curve radii while imparting a high-speed rotational driving to said bimetal knife.

The nucleotomy device according to the present invention includes a cutting tool whereof the torque cable is linked to the bimetal knife by means of a mechanical link making it possible on the one hand to screw said bimetal knife and on the other hand to fasten it to said torque cable by welding.

The nucleotomy device according to the present invention includes a cutting tool whereof the mechanical link is made up of a sleeve including a threaded inner bore at one of its ends designed to cooperate with a threaded part of the bimetal knife, while the other end of the sleeve extends by means of a shoulder with a small diameter housed inside the torque cable to be fastened to the latter by welding.

The nucleotomy device according to the present invention includes a tool holder that is made up of an elongated and hollow main body inside which the first and second connection means and the means for driving the cutting tool are arranged and guided, said main body being secured perpendicular to one of its ends to a first stationary handle inside which the adjustment means are housed, while a second elastically charged moving handle pivots around the stationary handle so as to be able to act on the driving means commanding the longitudinal translational and rotational movements of the blade cutting tool.

The nucleotomy device according to the present invention includes a tool holder whereof the first connection means are made up of a cylindrical linking sleeve fastened and guided inside the main body, said linking sleeve including a linking shaft cooperating on the one hand with an output shaft of the electric motor and on the other hand with the driving means to ensure the rotational driving of the cutting tool.

The nucleotomy device according to the present invention includes a tool holder whereof the second connection means are made up, at the free end of the main body of the tool holder, of two diametrically opposite notches respectively designed to receive, by snapping, locking tongues formed in the connection ring of the cutting tool.

The nucleotomy device according to the present invention includes a tool holder whereof the driving means are made up of a cylindrical linking sleeve guided in translation inside the main body and including, in its inner part, a freely rotating transmission shaft that cooperates with the linking shaft of the first connection means to ensure rotational driving of the cutting tool on the one hand, and on its outer periphery and across from one another, guide fingers, respectively passing through an oblong slot formed in the main body of the tool holder, said guide fingers emerging outside the main body each to be housed inside an oblong slot respectively formed in the branches of a fork secured to the moving handle to ensure the translational movement of the cutting tool on the other hand. The nucleotomy device according to the present invention includes a tool holder whereof the linking sleeve of the drive means includes, in the extension of its transmission shaft and across from the first connection means, a transmission bore making it possible to receive the linking element of the cutting tool so as to impart the rotational movements coming from the electric motor to the latter.

The nucleotomy device according to the present invention includes a tool holder whereof the adjustment means are made up of a threaded screw guided in rotation inside the stationary handle of the tool holder and secured at one of its ends to a knob making it possible to position the slider at graduations attached on either side of an oblong opening formed in the upper part of said stationary handle, said screw cooperates with a lever connected to an axis of rotation around which the moving handle pivots, such that the rotational driving of the screw makes it possible to position the lever in different angular positions so as to be able to act on the pivoting travel of the moving handle and, consequently, to limit the translational movements of the driving means.

The nucleotomy device according to the present invention includes a tool holder whereof the retraction means are made up of a strike guided in its pivoting on the main body of the tool holder so as to be able to move a lever secured to said strike and the free end of which is housed inside a bore formed in said main body.

The nucleotomy device according to the present invention includes injection and suction means that are made up of an injection circuit in which physiological serum flows penetrating inside the nuclear space Es being formed and a suction circuit making it possible to recover the physiological serum and the debris produced by the bimetal knife of the cutting tool.

The nucleotomy device according to the present invention includes injection and suction means whereof the injection circuit is connected to an injection pump supplied with physiological serum, while the suction circuit is connected to a suction pump including a reservoir for recovering physiological serum and debris.

The nucleotomy device according to the present invention includes an electric rotational driving motor and injection and suction means that are connected to a control housing driven by the user using control pedals.

The nucleotomy device according to the present invention includes injection and suction means that are made up of a linking connector fastened on the one hand on the end of a hinged tube implanted beforehand in the body of the corresponding vertebra Va, and on the other hand on the main body of the tool holder.

The nucleotomy device according to the present invention includes a linking connector whereof the fastening means are made up of a latch cooperating with the fastening head of the hinged tube on the one hand and a hinged clamp snapping around the main body of the tool holder on the other hand.

The nucleotomy device according to the present invention includes a linking connector comprising connecting outlets for fastening injection and suction circuits.

BRIEF DESCRIPTION OF THE DRAWINGS

The following description in light of the appended drawings, provided as non-limiting examples, will make it possible to better understand the invention, the features thereof, and the advantages it may procure.

DETAILED DESCRIPTION OF THE INVENTION

Figure 1:
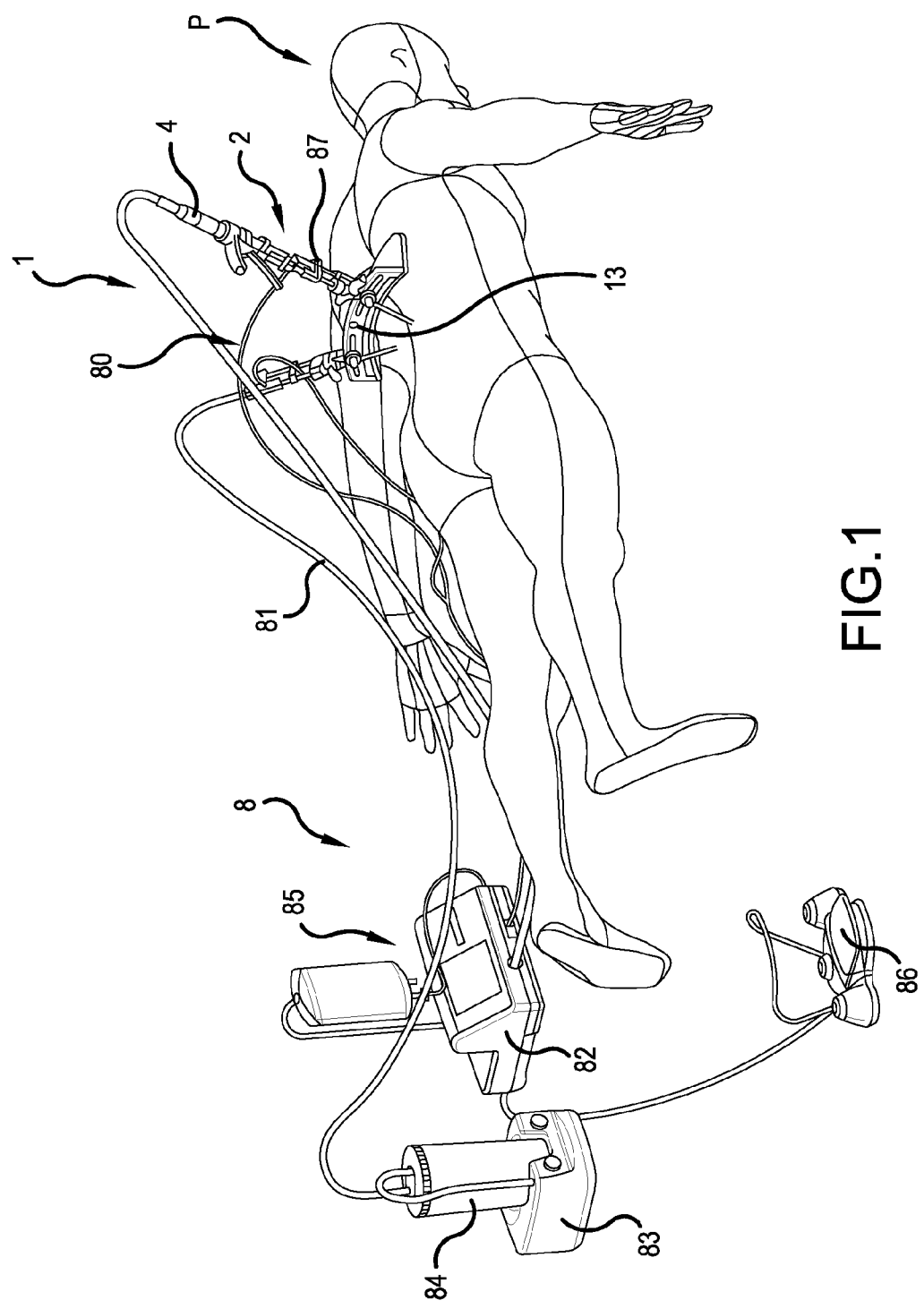
FIGS. 1 to 3 are diagrammatic perspective views illustrating the nucleotomy device according to the present invention.
Figure 2:
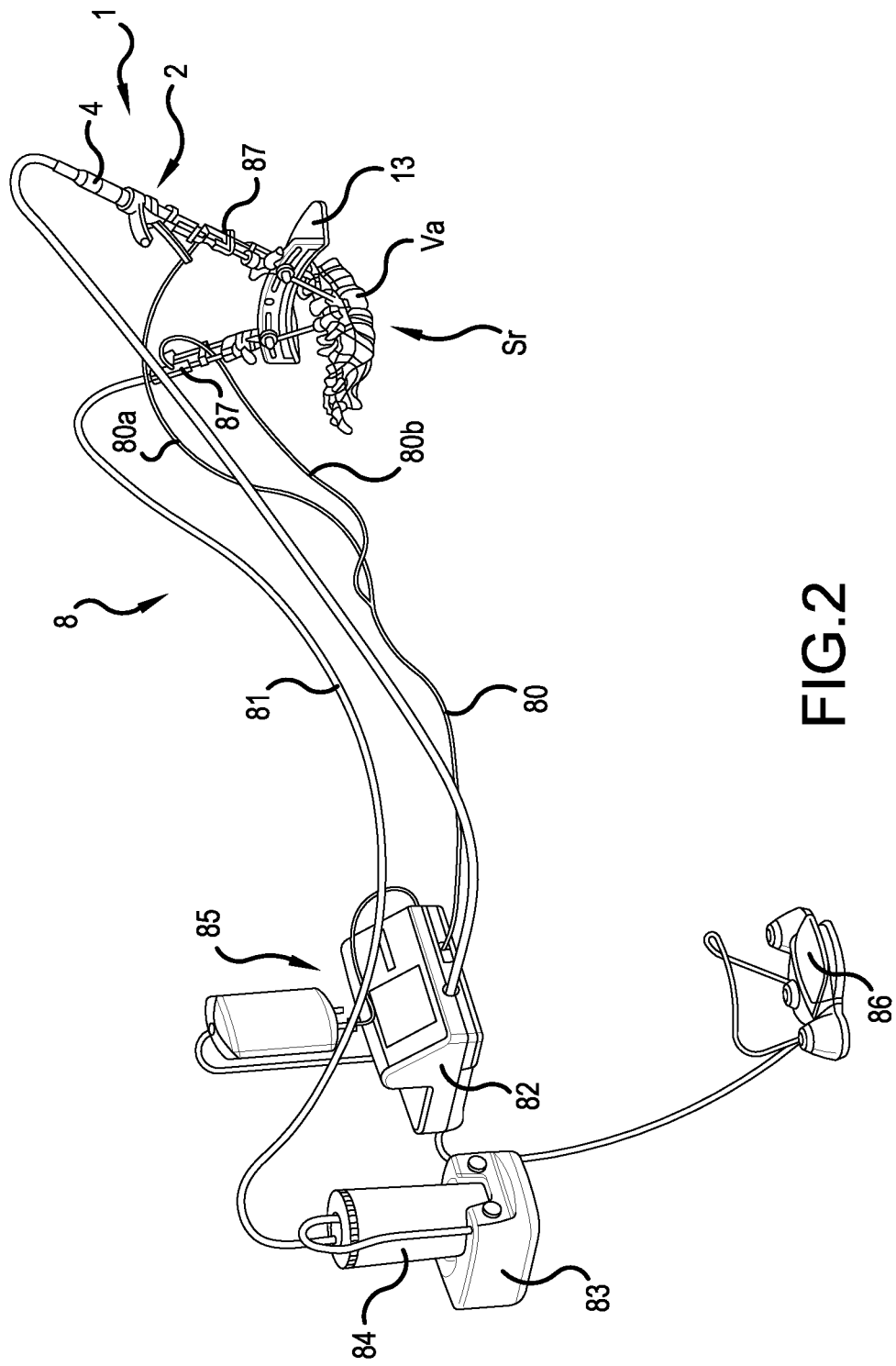
Figure 3:
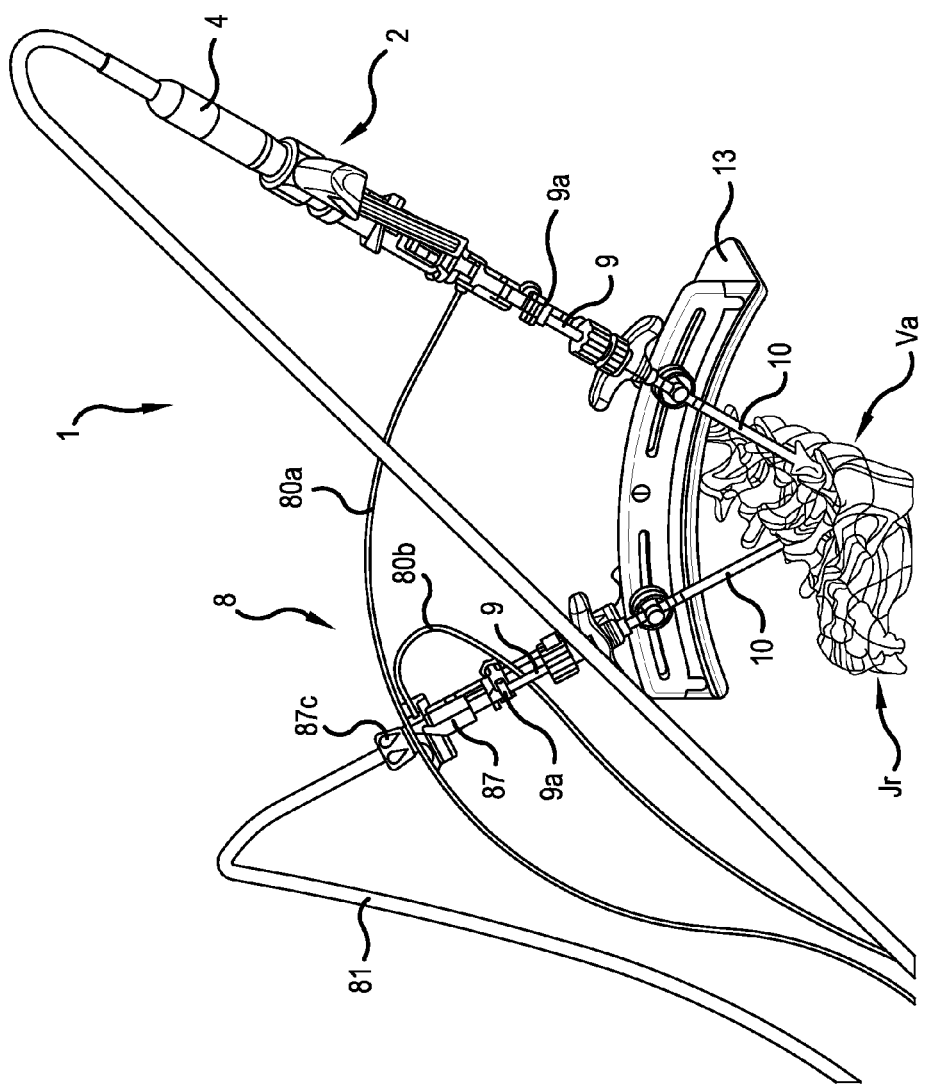

FIGS. 1 to 3 show a nucleotomy device 1 according to the present invention making it possible, from piercings Pr made beforehand, using a transosseous approach in the body of a vertebra Va of a spinal segment Sr of the patient P, to produce a nuclear space Es in an intervertebral disc Di.

The nucleotomy device 1 comprises an angular adjustment holder 13 fastened on the outer part of the body of the patient P and on which two cannulas 10 are positioned and fastened anchored in the body of the corresponding vertebra Va of the spinal segment Sr.

The two cannulas 10 respectively cooperate with a hinged tube 9 comprising a fastening head 9a making it possible, by means of a linking connector 87, to place and fasten a gun-shaped tool holder 2 comprising connection means 5 and driving means 7 respectively ensuring the placement and the rotational and longitudinal translational driving of a cutting tool 6.

The nucleotomy device 1 comprises injection and suction means 8 making it possible to evacuate debris from the nucleus resulting from cutting during its formation inside the intervertebral disc Di.

The injection and suction means 8 are made up of an injection circuit 80 in which physiological serum flows penetrating inside the nuclear space Es being formed and a suction circuit 81 making it possible to recover physiological serum and debris produced by the bimetal knife 6a of the cutting tool 6.

The injection circuit 80 is connected to an injection pump 82 supplied with physiological serum, while the suction circuit 81 is connected to a suction pump 83 including a reservoir 84 for recovering physiological serum and debris produced by the bimetal knife 6a of the cutting tool 6.

The injection and suction means 8 are connected to a control housing 85 controlled by the user using control pedals 86.

The injection and suction means 8 include first and second linking connectors 87 respectively fastened on the fastening head 9a of the first and second hinged tubes 9 inserted inside the first and second cannulas 10 previously anchored in the body of the corresponding vertebra Va of the spinal segment Sr.

Figure 11:
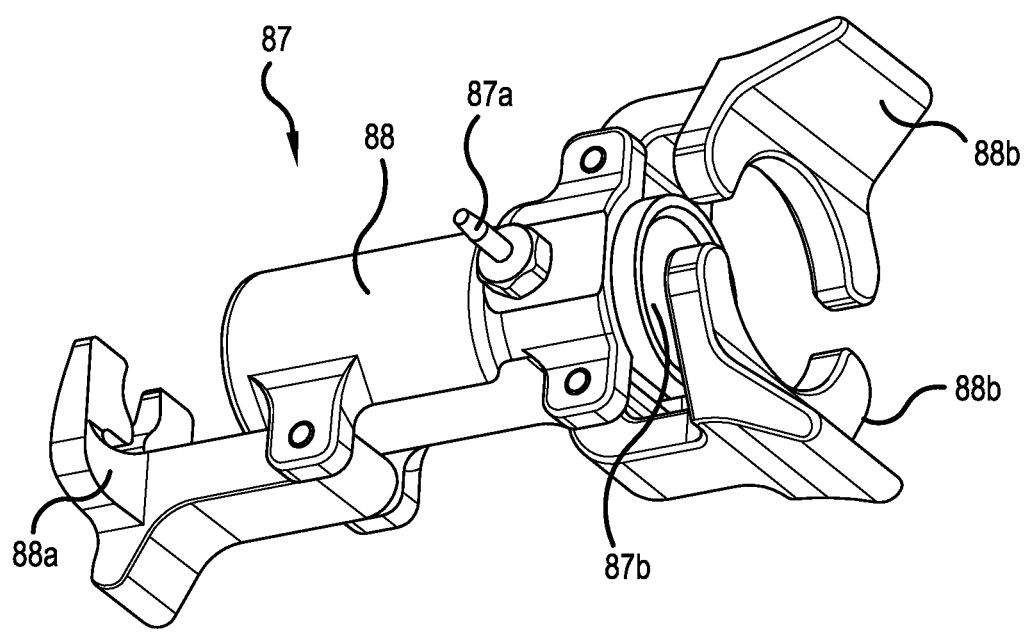
FIGS. 11 to 13 are views illustrating the linking connector ensuring fastening of the gun-shaped main body on a hinged tube guided inside the vertebral body of the spinal segment.
Figure 12:
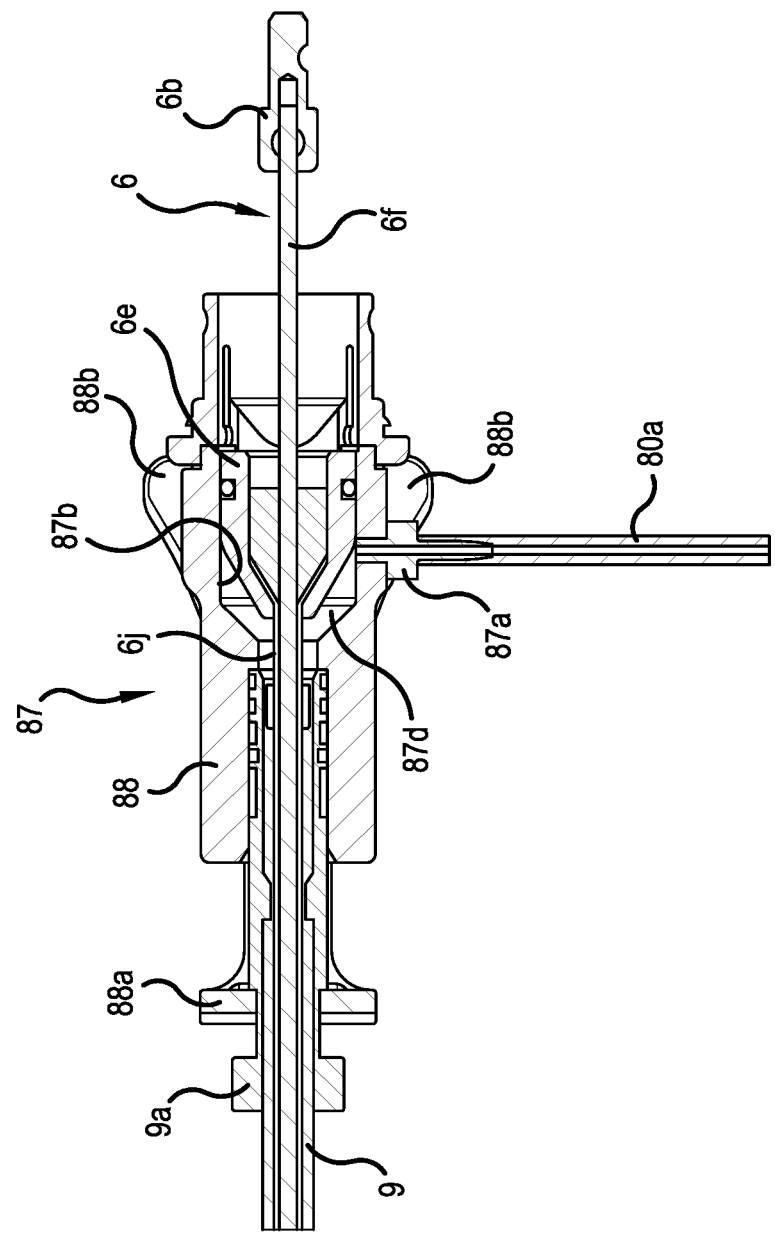
Figure 13:
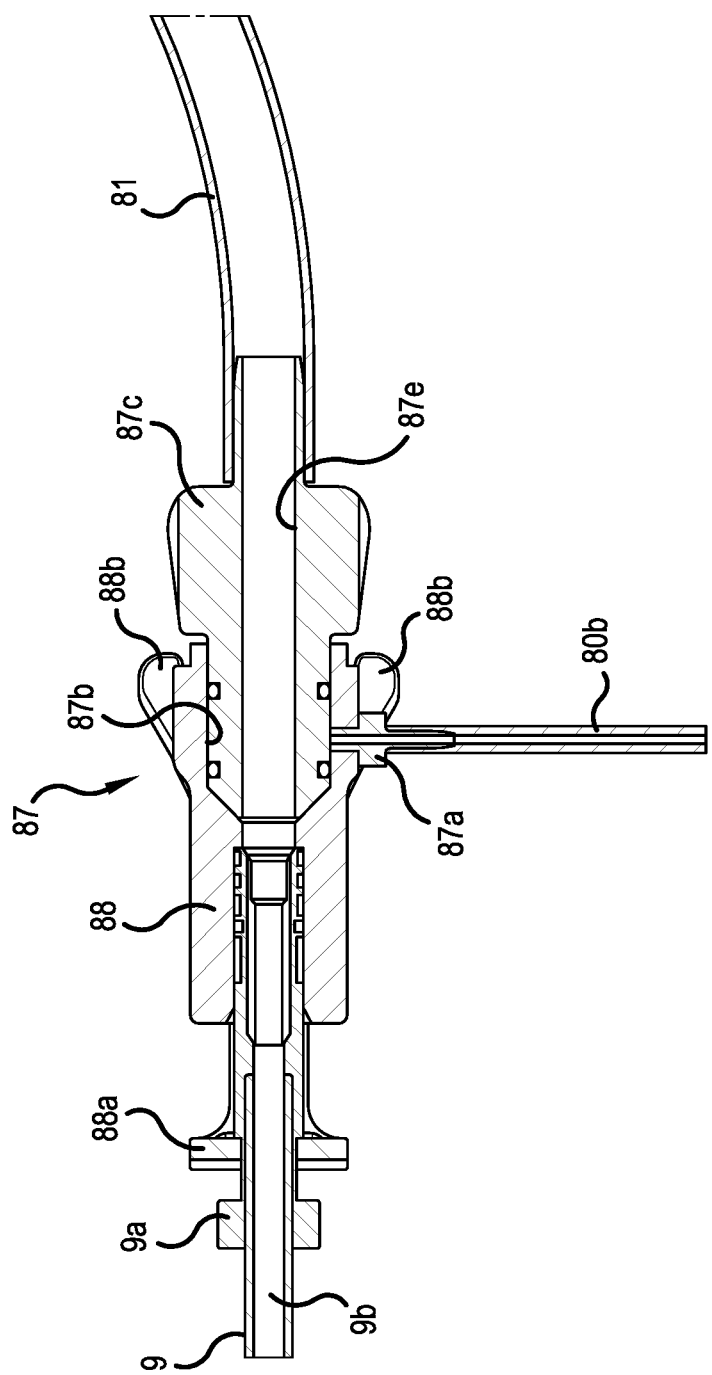

FIGS. 11 to 13 show the linking connector 87, which is made up of a hollow cylindrical sleeve 88 including fastening means that are made up on the one hand of a latch 88a cooperating with the fastening head 9a of the corresponding hinged tube 9 and on the other hand of a hinged clamp 88b snapping around the main body 2a of the tool holder 2.

The fastening means are also made up, across from the latch 88a, of a hinged clamp 88b having two jaws extending the cylindrical sleeve and, in the locking position, snapping around the gun-shaped tool holder 2.

The cylindrical sleeve forming the linking connector 87 includes a first plug terminal 87a making it possible to connect injection hoses 80a, 80b coming from a Y separation of the injection circuit 80 of the injection and suction means 8.

The cylindrical sleeve forming the linking connector 87 includes a second plug terminal 87b either allowing the connection, by means of a connection stopper 87c of the suction circuit 81, of the injection and suction means 8, or the placement, using a connection ring 6e, of the cutting tool 6 arranged on the main body 2a of the tool holder 2.

The plug terminals 87a, 87b are positioned on the cylindrical sleeve in diametrically opposite directions so as to respectively emerge at different levels inside the hinged tube 9 on which the linking connector 87 is fastened.

In FIG. 12, the linking connector 87 is shown arranged on the first hinged tube 9 and whereof the first plug terminal 87a for example cooperates with the hose 80a of the injection circuit 80, while the second plug terminal 87b sealably cooperates with the connection ring 6e of the cutting tool 6.

In this configuration, it will be noted that the first plug terminal 87a emerges in a free space 87d formed between the inner face of the second plug terminal 87b and the outer face of the connecting ring 6e of the cutting tool 6.

Thus, the physiological serum coming from the injection pump 82 is inserted into the linking connector 87 via the hose 80a and the first plug terminal 87a so as to pass through the free space 87d and flow inside the first hinged tube 9, and more particularly between the inner face of a bore 9b and the outer face of a sheath 6j of the cutting tool 6 to emerge inside the nuclear space Es being formed.

FIG. 13 shows the linking connector 87 arranged on the second hinged tube 9 and whereof the first plug terminal 87a for example cooperates with the hose 80b of the injection circuit 80, while the second plug terminal 87b sealably cooperates with the connection stopper 87c, the inner bore 87e of which is linked to the suction circuit 81 of the injection and suction means 8.

In this configuration, one can see that the first plug terminal 87a is sealably obstructed by the connection stopper 87e so as to prevent the physiological serum coming from the injection pump 82 from flowing inside the second hinged tube 9.

However, it will be noted that the inner bore 87e of the connection stopper 87c cooperates across from the suction circuit 87 with the inner bore 9b of the second tube 9 so as to be able to suction the physiological serum located inside the nuclear space Es being formed.

Figure 4:
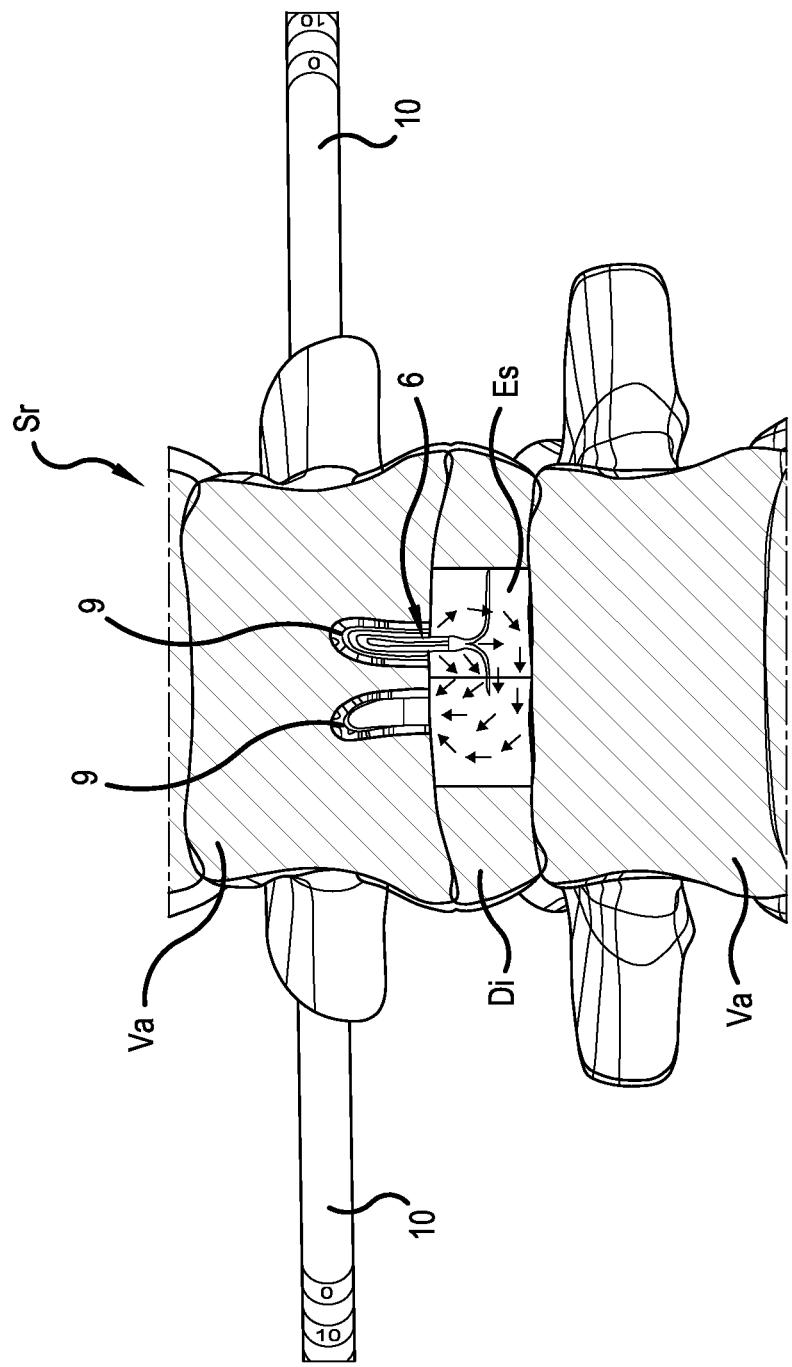
FIG. 4 is a cross-sectional view showing a spinal segment in which a nuclear space Es has been formed inside the intervertebral disc Di using the nucleotomy device according to the present invention.
Figure 5:
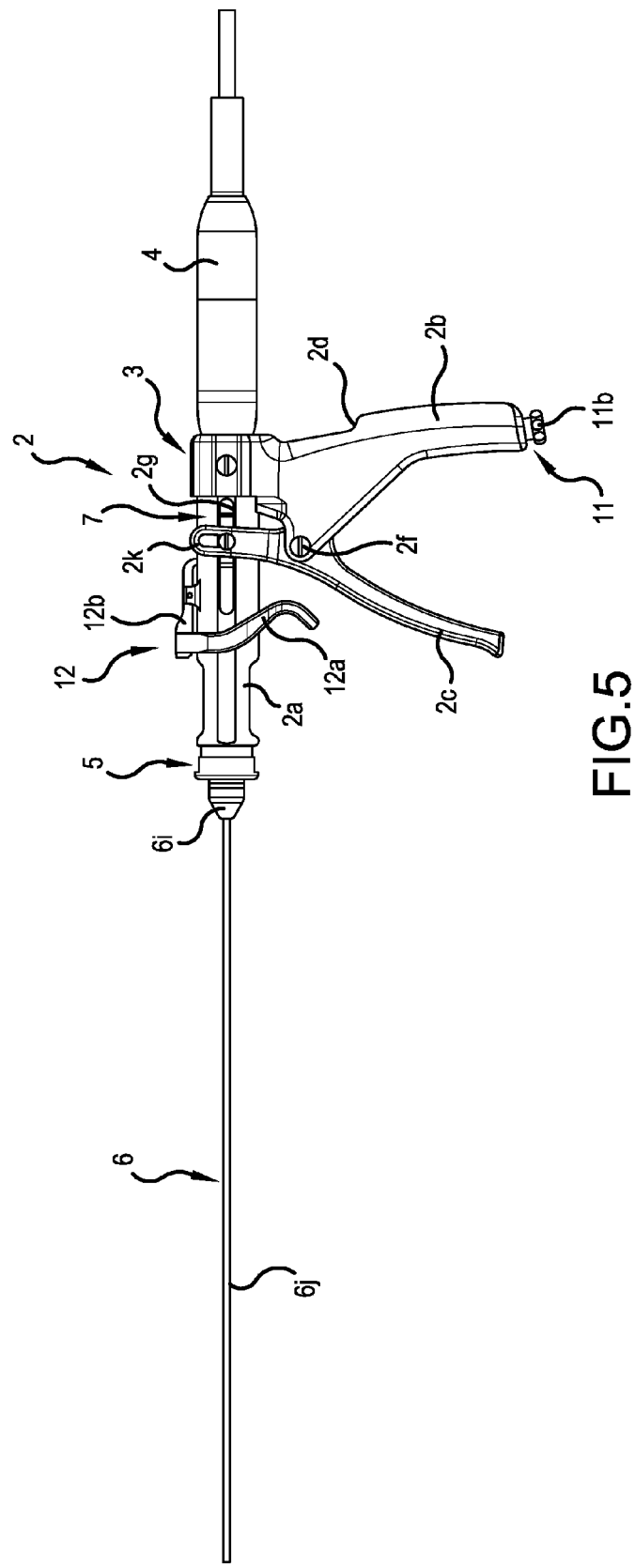
FIGS. 5 to 8 are perspective views showing the gun-shaped tool holder for the nucleotomy device, on which a blade cutting tool is arranged as well as driving means according to the present invention.
Figure 6:
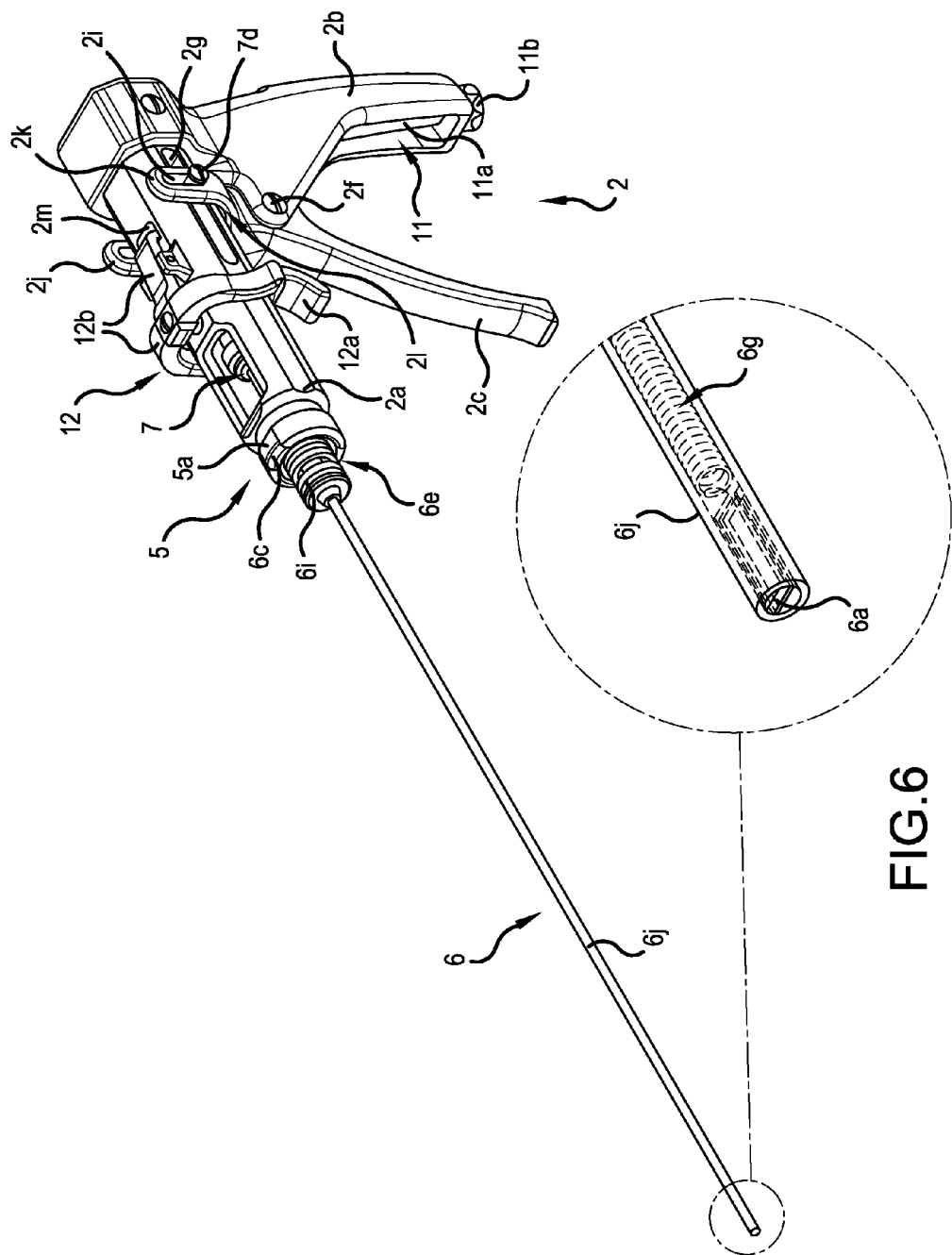
Figure 7:
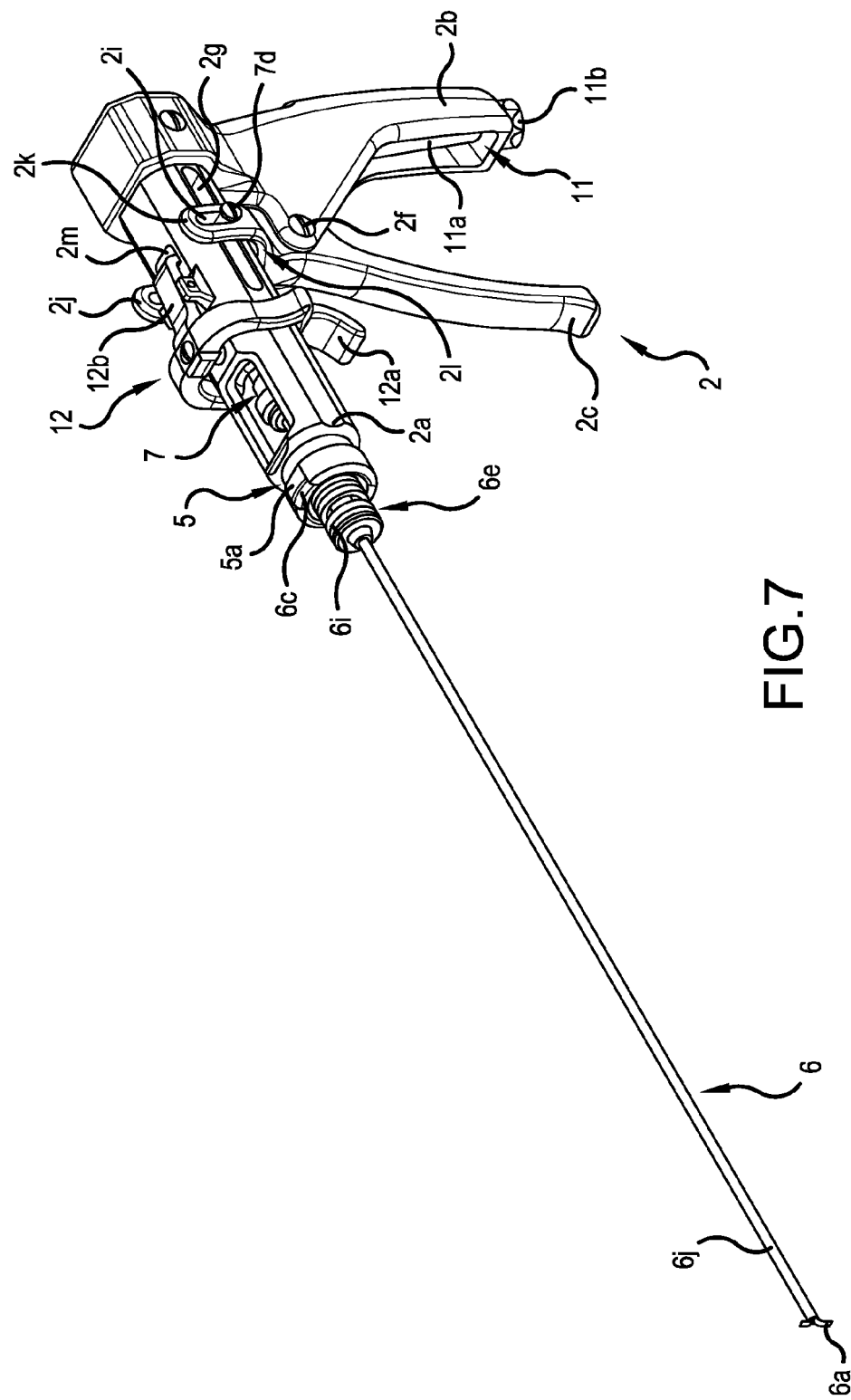

It will be noted that this particular arrangement allows the flow of the physiological serum introduced by the injection pump 82 in the injection circuit 80a of the first linking connector 87 and the recovery, after having passed through the nuclear space Es, of said physiological serum and the debris produced by the bimetal knife of the cutting tool 6 using the suction pump 83 connected to the suction circuit 81 of the second linking connector 87 (FIG. 4).

One can see that the physiological serum flows in a closed loop so as to enter through the first linking connector 87 arranged on the first hinged tube 9 and bearing the gun-shaped tool holder 2 to exit through the second linking connector 87 mounted on the second hinged tube 9 and that was previously obstructed by a stopper 87c.

It will be noted that the surgeon must proceed inversely with respect to the above description when the gun-shaped tool holder 2 is fastened on the second linking connector 87.

FIGS. 5 to 10 show the gun-shaped tool holder 2 of the nucleotomy device 1 making it possible to produce the nuclear space Es inside the intervertebral disc Di using the cutting tool 6.

The gun-shaped tool holder 2 is made up of an elongated hollow body 2a inside which first and second connection means 3 and 5 and the driving means 7 of the cutting tool 6 are arranged and guided.

The main body 2a of the gun-shaped tool holder 2 is secured perpendicularly at one of its ends to a first stationary handle 2b, inside which the adjustment means 11 are housed, while a second movable handle 2c that is elastically charged pivots around the stationary handle 2b so as to be able to act on the driving means 7 controlling the longitudinal translational and rotational movements of the blade cutting tool 6.

The first connection means 3 housed in the main body 2a of the gun-shaped tool holder 2 make it possible to place and fasten an electric rotational driving motor for imparting the rotational driving by means of the driving means 7 of the cutting tool 6.

The first connection means 3 are made up of a cylindrical linking sleeve 3a fastened inside the main body 2a of the gun-shaped tool holder 2 and above the stationary handle 2b.

The linking sleeve 3a makes it possible to receive the electric motor 4 by snapping such that its output shaft 4a cooperates with a linking shaft 3b axially guided inside the main body 2a of the gun-shaped tool holder 2. The linking shaft 3b cooperates with the driving means 7 to ensure the rotational driving of the cutting tool 6.

The electric rotational driving motor 4 is linked by means of an electrical cord to the control housing 85, which is controlled by the user by means of control pedals 86.

Figure 9:
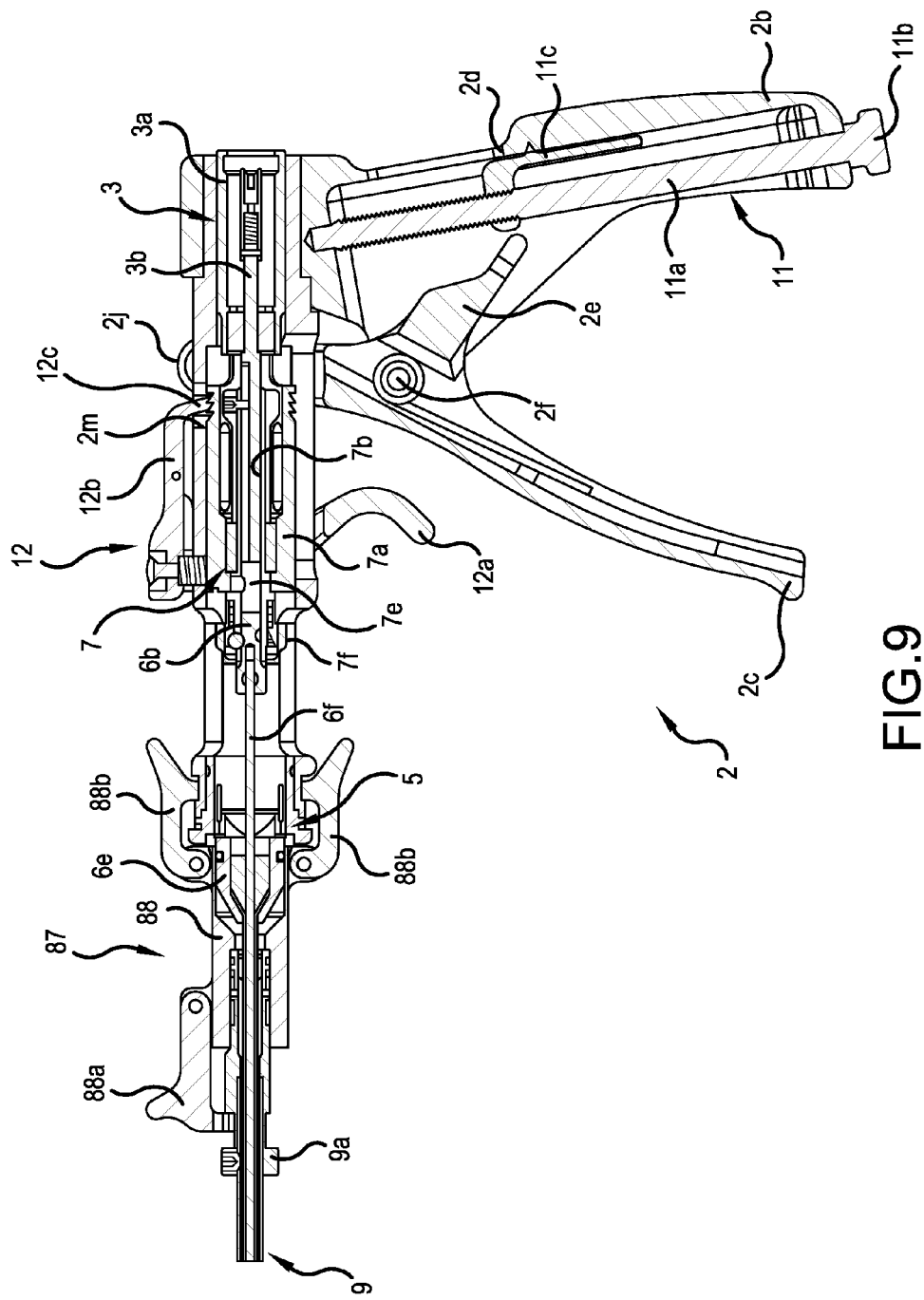
FIGS. 9 and 10 are cross-sectional views showing the gun-shaped tool holder of the nucleotomy device, on which a blade cutting tool and driving means according to the present invention are arranged.
Figure 10:
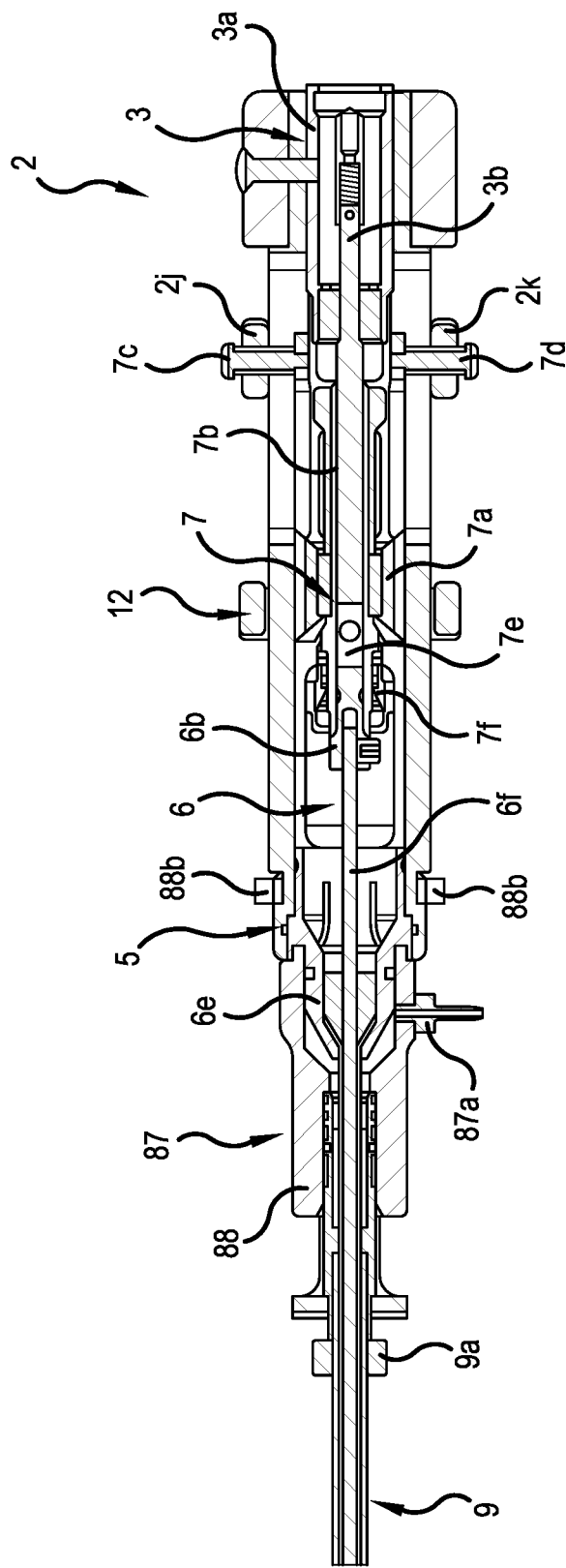

FIGS. 9 and 10 show the driving means 7, which are made up of the cylindrical linking sleeve 7a guided in translation inside the main body 2a of the gun-shaped tool holder 2.

The linking sleeve 7a includes, in its inner part, a freely rotating transmission shaft 7b that cooperates with the linking shaft 3b of the first connection means 3.

The linking sleeve 7a includes, on its outer periphery and across from one another, guide fingers 7c, 7d, respectively passing through an oblong slot 2g formed in the main body 2a of the gun-shaped tool holder 2.

The guide fingers 7c, 7d of the linking sleeve 7a emerge outside the main body 2a so as each to be housed inside an oblong slot 2h, 2i respectively formed in the branches 2j and 2k of a fork 21 secured to the moving handle 2c.

The linking sleeve 7a includes, in the extension of its transmission shaft 7b and across from the first connection means 3, a transmission bore 7e making it possible to receive a linking element 6b secured to the cutting tool 6 so as to transmit the rotational movements from the electric motor 4 thereto.

It will be noted that when the moving handle 2c is activated, the latter makes it possible, by means of its branches 2j and 2k extending above the axis of rotation 2f, to move the linking sleeve 7a secured to its transmission shaft 7b in translation inside the main body 2a to simultaneously impart the translational and rotational movements of the cutting tool 6 fastened to said main body 2a using the second connection means 5.

The second connection means 5 and the driving means 7 guided inside the main body 2a of the gun-shaped tool holder 2 respectively ensure the placement and the rotational and longitudinal translational driving of the cutting tool 6.

The second connection means 5 are formed at the free end of the main body 2a of the gun-shaped tool holder 2 by two diametrically opposite notches 5a, 5b respectively designed to receive, by snapping, the locking tongues 6c, 6d made in a connection ring 6e of the cutting tool 6.

Figure 14:
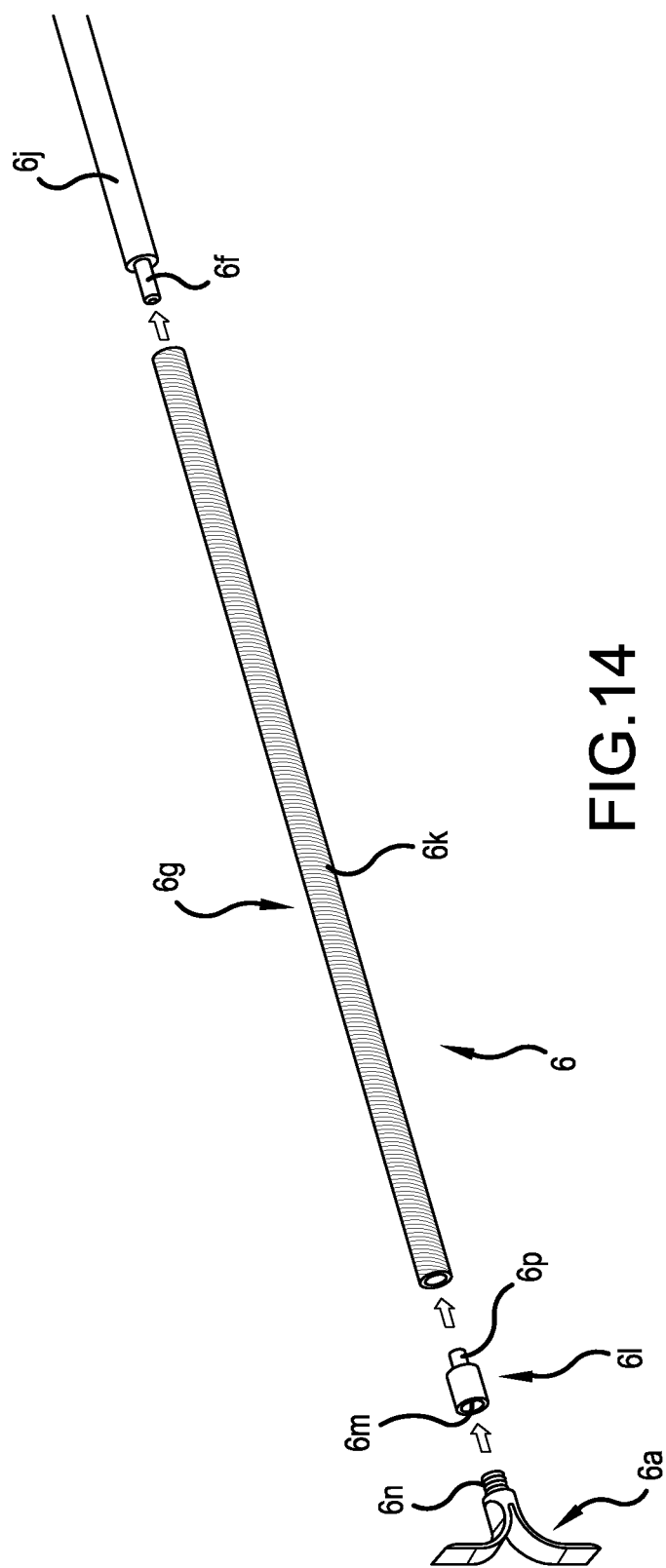
FIGS. 14 to 16 are views showing the cutting tool, and more particularly the arrangement of the flexible link between the bimetal knife and the metal rod according to the present invention.
Figure 15:
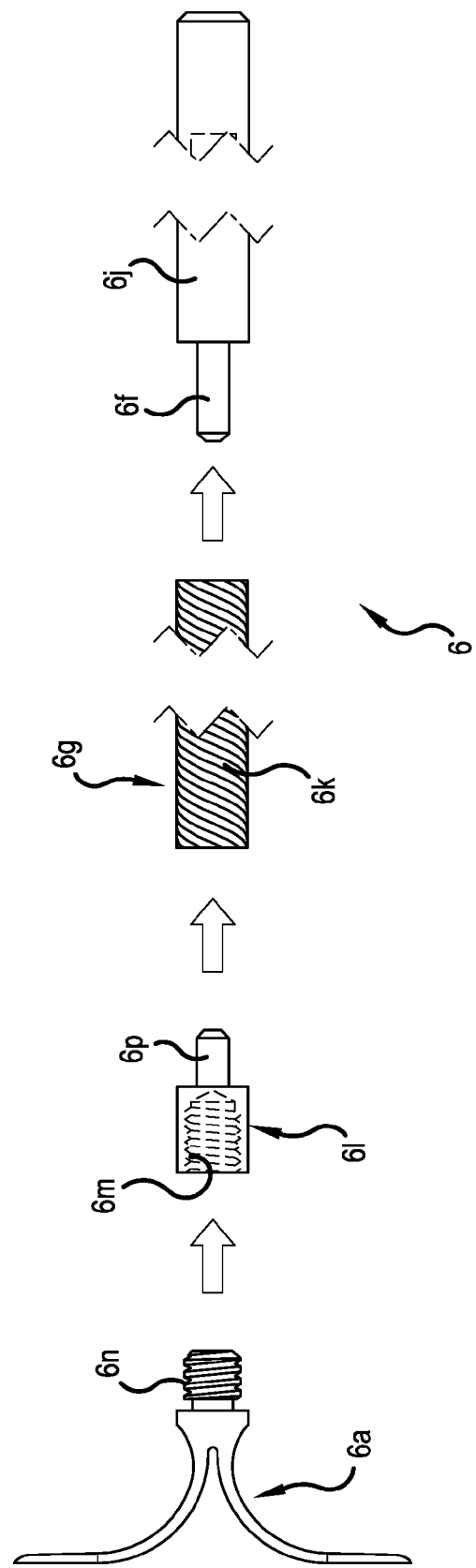
Figure 16:
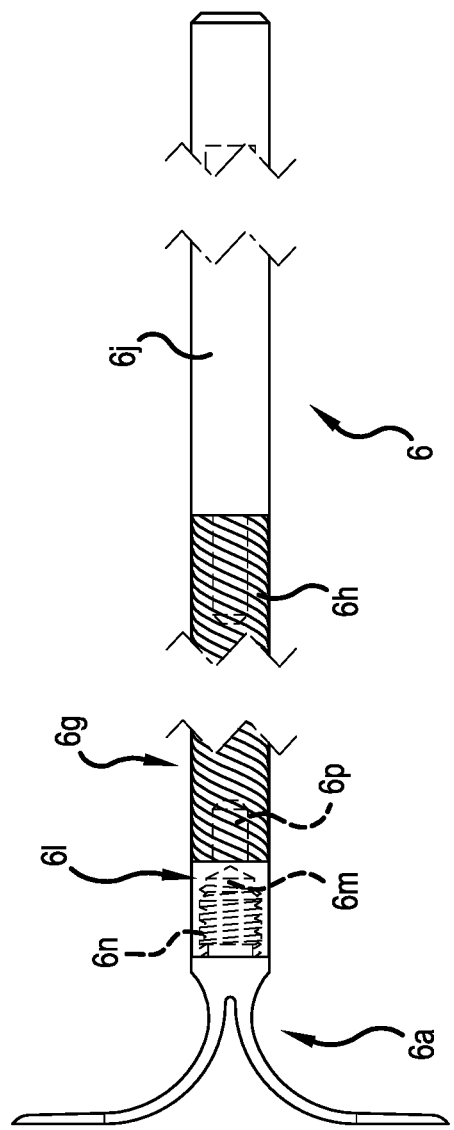

FIGS. 14 to 16 show the cutting tool 6 made up of a flexible metal rod 6f that is secured at one end thereof by means of a flexible link 6g of the bimetal knife 6a made from a deformable material, while the other end, after placement of the connection ring 6e, receives the linking element 6b, which is immobilized in translation on said metal rod by a clamping screw 6h.

The connection ring 6e cooperates with a clamping chuck 6i making it possible to place and retain a protective sheath 6j made from a plastic material and enveloping the flexible metal rod 6f and the flexible link 6g supporting the bimetal knife 6a.

The flexible link 6g making it possible to link one of the ends of the metal rod to the bimetal knife 6a is made from a deformable material, such that the cutting tool 6 can be deformed and follow small curve radii.

The flexible link 6g of the cutting tool 6 is made up of a torque cable 6k fastened to the bimetal knife 6a on the one hand and to the metal rod 6f on the other hand.

The torque cable 6k can deform to follow small curve radii while imparting a high-speed rotational driving to said bimetal knife 6a.

The torque cable 6k is linked to the bimetal knife 6a by means of a mechanical link 6l on the one hand allowing the screwing of said bimetal knife 6a and on the other hand fastening by welding of said torque cable 6k.

The mechanical link 6l is formed by a sleeve including, at one end thereof, a threaded inner bore 6m designed to cooperate with the threaded part 6n of the bimetal knife 6a, while the other end of the sleeve is extended by a shoulder 6p with a small diameter becoming housed inside the torque cable 6k to be fastened to the latter by welding.

The fastening by threaded link between the inner bore 6m and the threaded part 6n of the bimetal knife 6a is completed by a soldering link preventing any risk of loosening of the two threaded parts.

The torque cable 6k is fastened across from the bimetal knife 6a to the metal rod 6f. The metal rod 6f has a small outer diameter so as to be housed inside the torque cable 6k and fastened to the latter by soldering.

Figure 8:
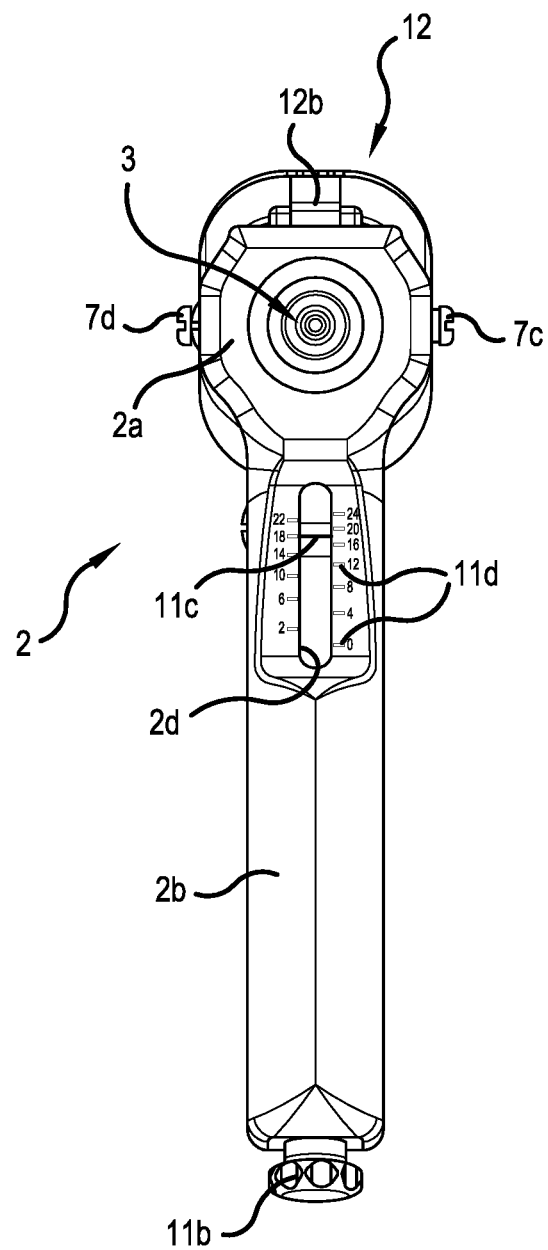

The nucleotomy device 1 includes adjusting means 11 that are made up of a threaded screw 11a guided in rotation inside the stationary handle 2b and secured at one of its ends to a knob 11b making it possible to position the slider 11c at graduations 11d etched on either side of an oblong opening 2d that are formed in the upper part of the stationary handle 2b (FIGS. 8 and 9).

The screw 11a cooperates with a lever 2e linked to an axis of rotation 2f around which the moving handle 2c pivots.

The rotational driving of the screw 11a makes it possible to position the lever 2e in different angular positions so as to be able to act on the pivoting travel of the moving handle 2c and consequently to limit the translational movements of the driving means 7.

The nucleotomy device 1 includes retraction means 12 making it possible to position the bimetal knife 6a of the cutting tool 6 inside the protective sheath 6j provided around the metal rod 6f (FIGS. 9 and 10).

In fact, the retraction means 12 make it possible to act on the flexible metal rod 6f by pulling on the latter so that the bimetal knife 6a, due to its super-elastic material, deforms and penetrates inside the protective sheath 6j.

The retraction means 12 are made up of a strike 12a whereof the pivoting is guided on the main body 2a of the tool holder 2 so as to be able to move a lever 12b secured to said strike 12a and whereof the free end 12c is housed inside a bore 2m formed in said main body 2a. In the idle position, the free end 12c of the lever 12b is in permanent contact with the linking sleeve 7a of the driving means 7 to which the cutting tool 6 is connected, limiting the backward travel of said sleeve, i.e., toward the first connection means of the nucleotomy device 1.

To allow the bimetal knife 6a to be inserted inside the protective sheath 6j, the surgeon must:

press on the strike 12a of the retraction means 12 so as to free the backward travel of the linking sleeve 7a of the driving means 7, pull on the moving handle 2c of the tool holder 2 to move the driving means 7 toward the rear of said tool holder 2, thereby driving the linking sleeve 7a to which the flexible metal rod 6f of the cutting tool 6 is connected in the same direction, making it possible to stress the bimetal knife 6a so that the latter penetrates inside the protective sheath 6j.

When the bimetal knife 6a of the cutting tool 6 mounted on the tool holder 2 of the nucleotomy device 1 is in the retracted position, the surgeon can insert the cutting tool 6 inside the cannula 9 so as to bring said cutting tool to the level of the intervertebral disc Di in which the nuclear space Es must be produced.

Operation of the Nucleotomy Device

Preparation of the Nucleotomy Device

The surgeon places and locks the two hinged tubes 9 inside the corresponding cannula 10, said cannula being fastened and anchored beforehand in the body of the vertebra Va of the spinal segment Sr so as to orient said cannula above the intervertebral disc Di in which the nuclear space Es must be formed.

He fastens a first and second linking connector 87 on each of the first and second hinge tubes 9, making it possible to place hoses forming the injection 80 and suction 81 circuits respectively linking the injection pump 82 and the suction pump 83 of the injection and suction means 8.

The electric motor 4 and the control panel 86 are also connected to the control housing 85 of the injection and suction means 8.

Figure 17:
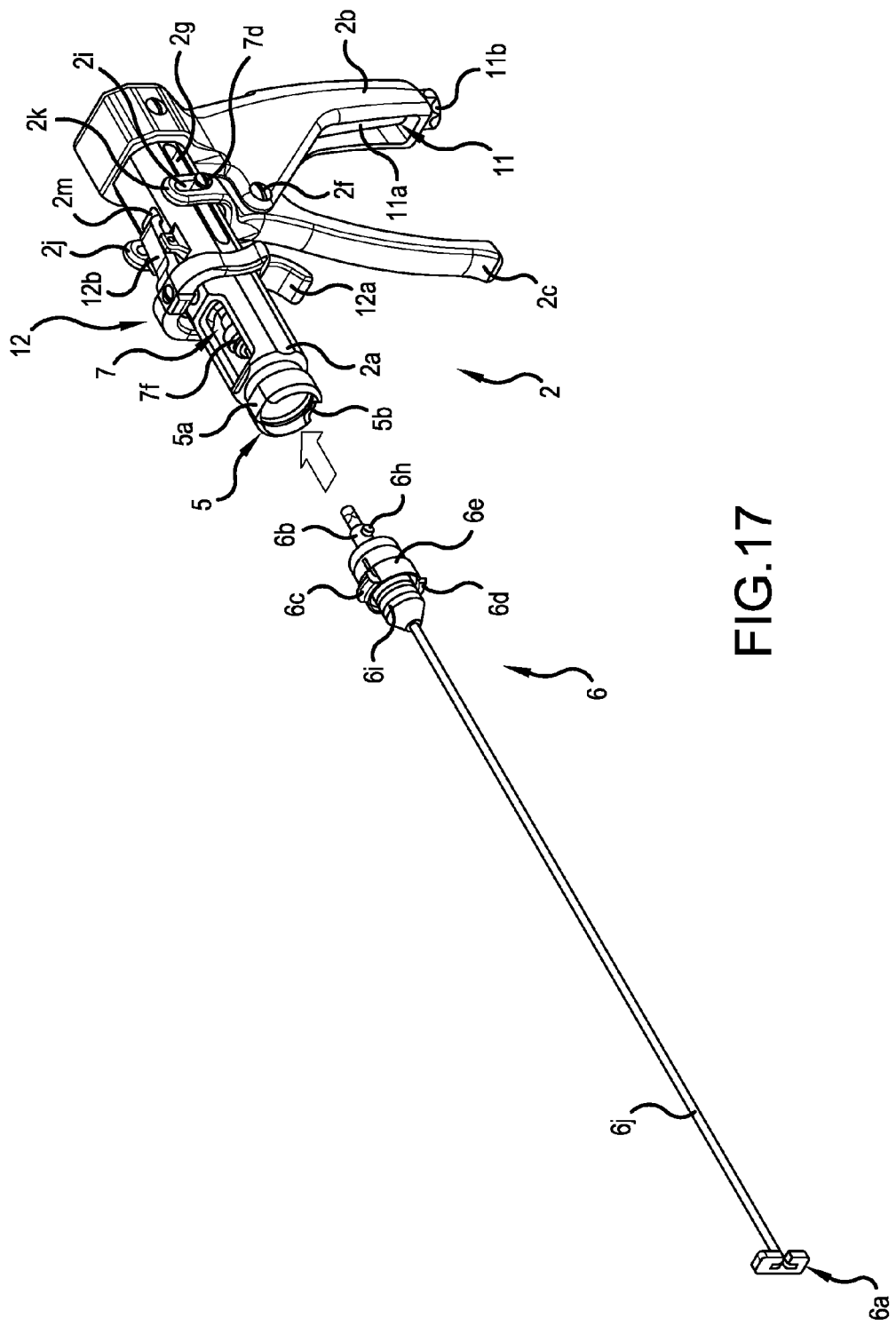
FIGS. 17 to 20 are views showing the different assembly steps of the gun-shaped tool holder and the blade cutting tool of the nucleotomy device according to the present invention.
Figure 18:
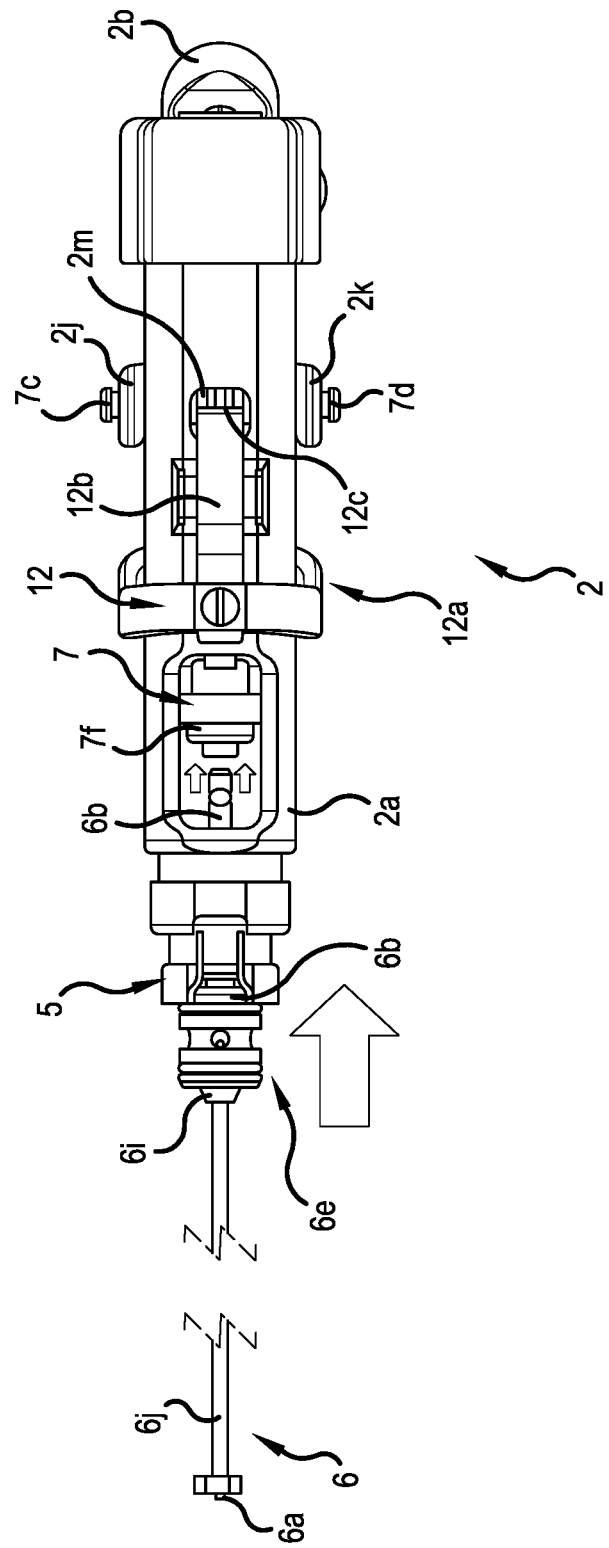
Figure 19:
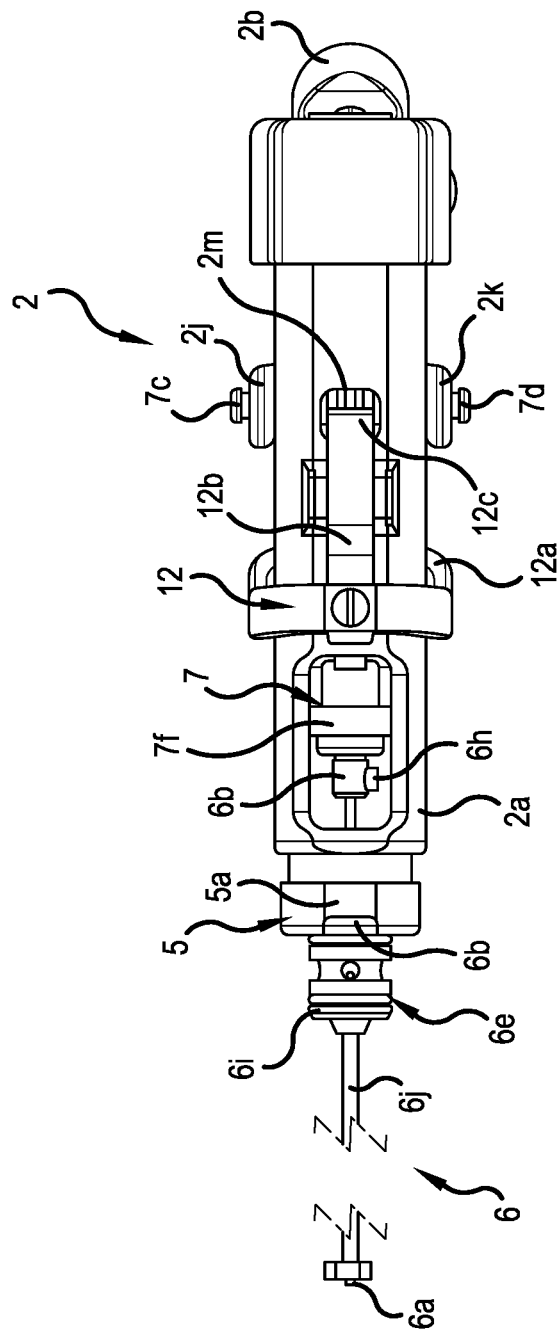

The surgeon chooses, from a set of cutting tools, a first cutting tool 6 whereof the bimetal knife 6a has a cutting diameter of 10 mm. The set of tools includes two other cutting tools 6, whereof the bimetal knife 6a respectively has a cutting diameter of 14 and 18 mm (FIGS. 17 to 19).

To that end, the surgeon presses on the outer ring 7f of the driving means 7 so as to be able to insert the linking element 6b inside the transmission bore 7e of said driving means. Simultaneously with the insertion of the linking element 6b, the connection ring 6e of the cutting tool 6 is connected to the second connection means 5 included by the main body 2a of the tool holder 2.

The locking of the cutting tool 6 on the tool holder 2 is definitively obtained when the surgeon releases the outer ring 7f of the driving means 7.

The surgeon must next protect the bimetal knife 6a of the cutting tool 6 before it is inserted in the first hinged tube 9. To that end, he presses on the strike 12a of the retraction means 12, then simultaneously pulls on the moving handle 2c of the tool holder 2 so as to move the metal rod 6f and the bimetal knife 6a inside the protective sheath 6j.

The strike 12a makes it possible, using its lever 12b, to lock the translation of the driving means 7 and to keep the bimetal knife 6a inside said protective sheath 6j, when the surgeon releases said strike 12a and said moving handle 2c.

Before the insertion of the cutting tool 6 and the first hinged tube 9, the surgeon adjusts the travel of the latter as a function of the height of the intervertebral disc Di. To that end, he turns the knob 11b of the adjustment means 11 so as to position the slider 11c on the graduation 11d corresponding to the height of said intervertebral disc Di.

The adjustment means 11 make it possible to act on the angular travel of the moving handle 2c, limiting the latter and therefore the translational movement of the driving means 7.

Lastly, the surgeon mounts the electric motor 4 on the main body 2a of the tool holder 2 so that the output shaft 4a of said motor cooperates with the linking shaft 3a of the first connection means of said tool holder 2.

Performance of the Nucleotomy

The surgeon inserts the cutting tool 6 assembled to the tool holder 2 inside the first hinged tube 9 previously positioned inside the first cannula 10. The cutting tool 6 is completely inserted until the tool holder 2 bears against the linking connector 87 previously fastened to the first hinged tube 9 using the latch 88a. The surgeon fastens the tool holder 2 on the linking connector 87 by closing the jaws of the hinged clamp 88b so that the latter cooperate with a circular peripheral slot 2n formed in the main body 2a.

On the other linking connector 87 mounted on the second hinged tube 9, the surgeon fastens a stopper 87c allowing the injection 80 and suction 81 circuit to operate as a closed circuit.

The surgeon then produces the nuclear space Es inside the intervertebral disc Di by gradually inserting the bimetal knife 6a of the tool 6.

Figure 20:
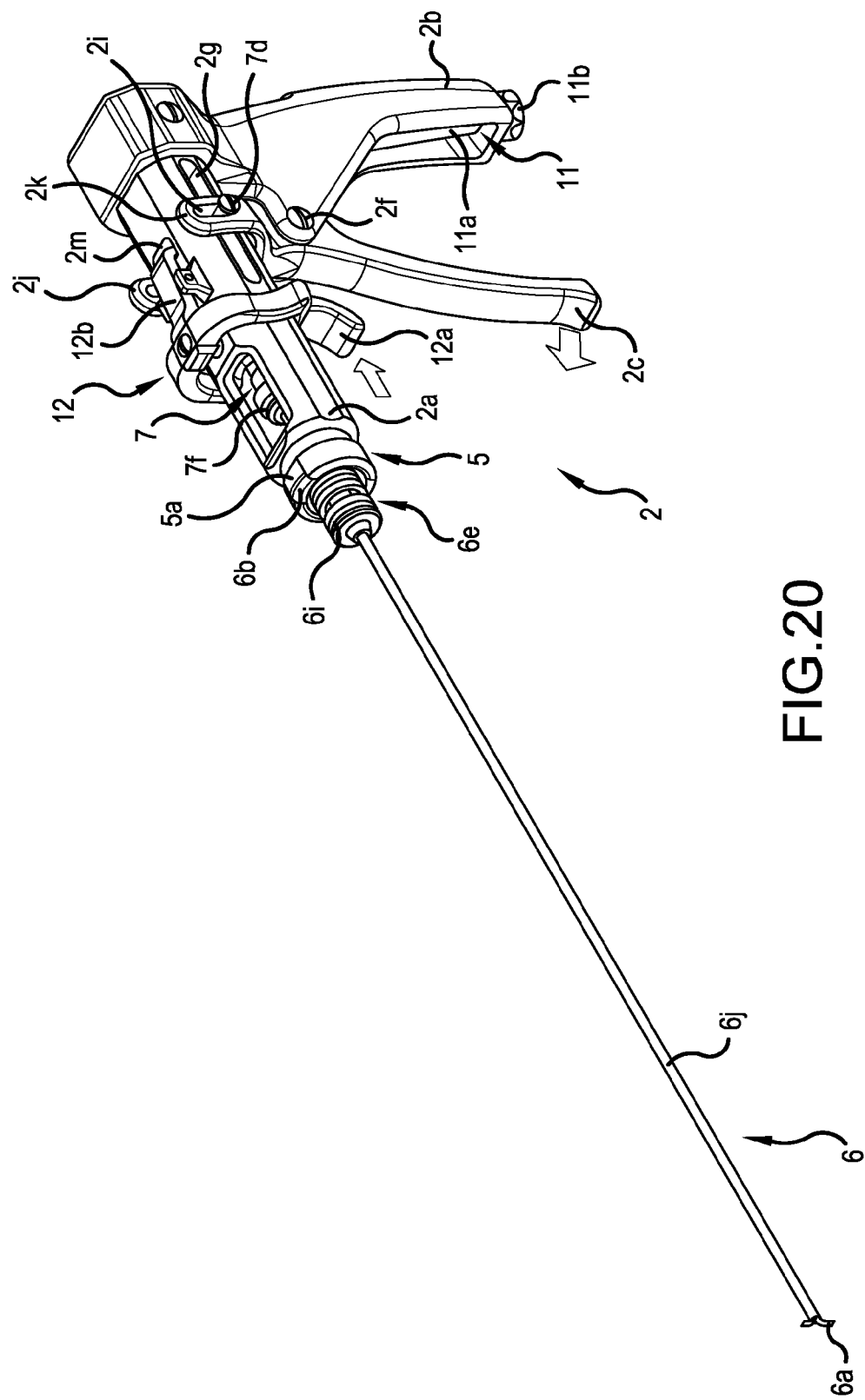

For that purpose, he simultaneously presses on the strike 12a and the moving handle 2c of the cutting tool 2 to release the driving means 7 and deploy the bimetal knife 6a outside the protective sheath 6j (FIG. 20).

He selects the nucleotomy protocol on the control housing 85 determining the speed of rotation and the torque of the cutting tool 6 and the startup of the injection 82 and suction 83 pumps.

Next, he presses on the control panel 86 to control the electric motor 4 and the rotation of the cutting tool 6.

He then performs successive "Press and Release" movements of the moving handle 2c of the tool holder 2 to perform gradual back-and-forth movements of the cutting tool 6, so that the bimetal knife 6a progresses inside the intervertebral disc Di and over the depth previously adjusted using the adjustment means 11.

When the nucleotomy with the cutting tool 6 having a diameter of 10 mm is complete, the surgeon releases the control panel 86, retracts the bimetal knife 6a inside the sheath 6j, and releases the tool holder 2 from the first linking connector 87 and removes said tool holder 2 from the first hinged tube 9.

Next, the surgeon unscrews the stopper 87c from the second connector 87 arranged on the second hinged tube 9 to be able to insert the tool holder 2, provided with its cutting tool 6 with a diameter of 10 mm, inside said tube to come into contact with the intervertebral disc Di.

He screws the stopper 87c on the first connector 87 arranged on the first hinged tube 9 from which he has just disassembled the tool holder 2, and inserts the tool holder 2 and its cutting tool 6 with a diameter of 10 mm inside the second hinged tube 9.

He positions and starts the injection 82 and suction 83 pumps so that the physiological liquid circulates in the right direction in the injection 80 and suction 81 circuits and in the nuclear space Es being produced.

The surgeon proceeds with the same manipulations of the tool holder 2 as those described in the preceding steps above to perform the nucleotomy.

When the nucleotomy with the cutting tool 6 having a diameter of 10 mm is complete, the surgeon releases the control panel 86, retracts the bimetal knife 6a inside the sheath 6j, and releases the tool holder 2 from the second linking connector 87 and removes said tool holder 2 from the second hinged tube 9.

Next, the surgeon takes another tool holder 2 secured to a cutting tool 6 whereof the cutting diameter is 14 mm, and inserts it into the second hinged tube 9 to fasten it on the second linking connector 87 to perform the same operations as previously described for the tool holder 2 secured to the cutting tool 6 whereof the cutting diameter is 10 mm.

Lastly, the surgeon takes another tool holder 2 secured to a cutting tool 6 whereof the cutting diameter is 18 mm, and inserts it into the first hinged tube 9 to fasten it on the first linking connector 87 to proceed with the same operations as previously described for the tool holder 2 secured to the cutting tool 6, whereof the cutting diameter is 10 mm.

When the nucleotomy with the cutting tool 6 having a diameter of 18 mm is complete, the surgeon releases the control panel 86, retracts the bimetal knife 6a inside the sheath 6j, and releases the tool holder 2 from the second linking connector 87 and removes said tool holder 2 from the second hinged tube 9.

The nucleotomy is complete and the nuclear space Es produced inside the intervertebral disc Di is ready to receive an implant.

It must also be understood that the preceding description was provided solely as an example and in no way limits the scope of the invention, and it would not be beyond the scope of the invention to replace the details of the described embodiments with any equivalent means.

The invention claimed is:

1. A nucleotomy device for producing a nuclear space in an intervertebral disc, using a transosseous approach in the body of a vertebra, the nucleotomy device comprising:
   an electric rotary driving motor with an output shaft;
   a tool holder provided with
   i) a blade cutting tool that produces the nuclear space in the intervertebral disc, said blade cutting tool being comprised of
      a) a double blade knife made from an elastic material, the double blade knife being comprised of a base and two, spaced apart blades extending from the base,
      b) a flexible metal rod enclosed in a plastic protective sheath, the flexible metal rod having a first end and an opposite, second end,
      c) a flexible link that links the first end of the flexible metal rod to the base of the knife,
      d) a linking element, and
      e) a connection ring,
   ii) a driving means connected, via the linking element, to the second end of the metal rod,
   the driving means imparting rotational and longitudinal translational movements to the cutting tool,
   iii) a first connection means that accepts and fastens to the output shaft of the electric rotary driving motor, and
   iv) a second connection means that accepts the blade cutting tool, wherein the connection ring cooperates with the second connection means to immobilize said cutting tool on said tool holder; and an injection and suction means that evacuate debris from the produced nuclear space in the intervertebral disc.

2. The nucleotomy device according to claim 1, further comprising an adjustment means housed in the tool holder, the adjustment means limiting translational travel of the cutting tool.

3. The nucleotomy device according to claim 2, wherein the tool holder is further made up of an elongated and hollow main body inside which the first and second connection means and the driving means are arranged and guided, said main body being secured perpendicular at one end to a stationary handle inside which the adjustment means are housed, while an elastic moving handle pivots around the stationary handle so as to be able to act on the driving means commanding the longitudinal translational and rotational movements of the blade cutting tool.

4. The nucleotomy device according to claim 3, wherein the first connection means are made up of a cylindrical linking sleeve fastened and guided inside the main body, said linking sleeve including a linking shaft cooperating with the output shaft of the electric rotary driving motor and with the driving means to provide the rotational driving of the cutting tool.

5. The nucleotomy device according to claim 4, wherein,
the driving means are made up of a cylindrical linking sleeve guided in translation inside the main body and including, in an inner part, a freely rotating transmission shaft that cooperates with the linking shaft of the first connection means to provide rotational driving of the cutting tool, and guide fingers, respectively passing through an oblong slot formed in the main body of the tool holder, said guide fingers emerging outside the main body each to be housed inside an oblong slot respectively formed in the branches of a fork secured to the moving handle to ensure the translational movement of the cutting tool.

6. The nucleotomy device according to claim 5, wherein the linking sleeve includes, in an extension of the transmission shaft and across from the first connection means, a transmission bore that receives the linking element of the cutting tool so as to impart the rotational movements coming from the electric rotary driving motor to the cutting tool.

7. The nucleotomy device according to claim 2, wherein,
the tool holder is further made up of a hollow main body,
an oblong opening is formed in an upper part of a stationary handle secured to the hollow main body,
the adjustment means comprise a threaded screw located inside the stationary handle,
the threaded screw is secured at one end to a knob to allow positioning of a slider at graduations located on either side of the oblong opening,
wherein said screw cooperates with a lever connected to an axis of rotation,
wherein a moving handle pivots around the axis of rotation such that the rotational driving of the screw positions the lever in different angular positions so as to be able to act on the pivoting travel of the moving handle and, consequently, to limit the translational movements of the driving means.

8. The nucleotomy device according to claim 1, further comprising a means for retracting the cutting tool so that the knife of the cutting tool is inside the protective sheath.

9. The nucleotomy device according to claim 8, wherein,
a main body of the tool holder includes a bore,
the retraction means are made up of a strike,
a lever is secured to said strike, the lever having a free end housed inside the bore of said main body, and
the strike pivots on the main body of the tool holder so as to move the lever secured to said strike and the free end of the lever which is housed inside the bore formed in said main body.

10. The nucleotomy device according to claim 1, further comprising a clamping chuck, wherein the connection ring cooperates with the clamping chuck to place and retain the protective sheath around the flexible metal rod.

11. The nucleotomy device according to claim 1, wherein the flexible link of the cutting tool is made up of a torque cable fastened to the base of the knife and to the metal rod, said torque cable being able to deformed to follow a curved path while imparting a rotational driving to said knife.

12. The nucleotomy device according to claim 11, wherein the torque cable is mechanically linked and welded to the base of the knife.

13. The nucleotomy device according to claim 12, wherein the mechanical link is made up of a sleeve including a threaded inner bore at one end thereof, the one end of the sleeve cooperating with a threaded part of the knife, while the other end of the sleeve extends by a shoulder with a diameter housed inside the torque cable.

14. The nucleotomy device according to claim 1, wherein the tool holder is made up of an elongated and hollow main body inside which the first and second connection means and the driving means are arranged and guided, said main body being secured perpendicular at one end to a stationary handle inside which the adjustment means are housed, while an elastic moving handle pivots around the stationary handle so as to act on the driving means commanding the longitudinal translational and rotational movements of the blade cutting tool, and the second connection means are made up, at the free end of the main body of the tool holder, of two diametrically opposite notches respectively designed to receive, by snapping, locking tongues formed in the connection ring of the cutting tool.

15. The nucleotomy device according to claim 1, wherein the injection and suction means are made up of an injection circuit in which physiological serum flows penetrating inside the nuclear space being formed and a suction circuit making it possible to recover the physiological serum and the debris produced by the knife of the cutting tool.

16. The nucleotomy device according to claim 15, wherein the injection circuit is connected to an injection pump supplied with physiological serum, while the suction circuit is connected to a suction pump including a reservoir for recovering physiological serum and debris.

17. The nucleotomy device according to claim 1, wherein the electric rotary driving motor and injection and suction means are connected to a control housing, the control housing being driven by control pedals operated by a user.

18. The nucleotomy device according to claim 1, wherein the injection and suction means are made up of a linking connector fastened on the end of a hinged tube and on a main body of the tool holder.

19. The nucleotomy device according to claim 18, wherein the linking connector includes fastening means that are made up of i) a latch cooperating with a fastening head of the hinged tube and ii) a hinged clamp snapping around the main body of the tool holder.

20. The nucleotomy device according to claim 18, wherein the linking connector comprises connecting outlets for respectively fastening to a hose of the injection circuit and to a hose of the suction circuit.

21. The nucleotomy device according to claim 1, wherein,
the knife base includes a threaded part,
the flexible link is comprised of i) a torque cable fastened to the metal rod and ii) a sleeve, the sleeve having a threaded inner bore at a first end thereof and an extended shoulder at a second end thereof, the threaded inner bore being screwed on the threaded part of the base of the knife, and the extended shoulder being housed inside the torque cable, and
said torque cable is deformable to follow a curved path while imparting a rotational driving to said knife.

* * * * *